United States Patent [19]
Komai et al.

[11] Patent Number: 5,821,062
[45] Date of Patent: Oct. 13, 1998

[54] OLIGONUCLEOTIDE FOR USE IN CHECKING PRESENCE OR ABSENCE OF MUTATION IN HUMAN-DERIVED CYTOCHROME P450IIC18 GENE

[75] Inventors: Koichiro Komai, Kawanishi; Hideo Kaneko; Iwao Nakatsuka, both of Kobe, all of Japan

[73] Assignee: Sumitomo Chemical Company, Limited, Osaka-fu, Japan

[21] Appl. No.: 716,459

[22] PCT Filed: Mar. 28, 1995

[86] PCT No.: PCT/JP95/00570

§ 371 Date: Nov. 5, 1996

§ 102(e) Date: Nov. 5, 1996

[87] PCT Pub. No.: WO95/26415

PCT Pub. Date: Oct. 5, 1995

[30] Foreign Application Priority Data

Mar. 29, 1994 [JP] Japan .................................. 6-059385
Mar. 29, 1994 [JP] Japan .................................. 6-059386

[51] Int. Cl.[6] .............................. C12Q 1/68; C12P 19/34; C07H 21/02; C07H 21/04
[52] U.S. Cl. ............................ 435/6; 435/91.1; 536/23.1; 536/24.31; 536/24.33
[58] Field of Search .............................. 536/23.1, 24.31, 536/24.33; 436/94; 435/6, 91.1

[56] References Cited

U.S. PATENT DOCUMENTS 5,225,326  7/1993  Bresser et al. ............................... 435/6

FOREIGN PATENT DOCUMENTS 4-320700  11/1992  Japan .
WO91/12343  8/1991  WIPO .

OTHER PUBLICATIONS

Romkes et al, Biochemistry, vol. 30, pp. 3247–3255 (1991).
Romkes et al, Biochemistry, vol. 32, No. 5, Corrections, p. 1390 (1993).
Weisgraber et al, Biochemical and Biophysical Research Communications, vol. 157, No. 3, pp. 1212–1217 (1988).
Hixson et al, Journal of Lipid Research, vol. 31, pp. 545–548 (1990).
Nature Genetics, vol. 5, No. 2, Oct. 1993, pp. 111–117, XP000615290, M. Grompe, *The Rapid Detection of Unknown Mutations in Nucleic Acids*.
Molecular Pharmacology, vol. 43, No. 2, Feb. 1993, pp. 234–239, XP000613062, L.S. kaminsky et al., *Correlation of Human Cytochrome P4502C Substrate Specificities With Primary Structure: Warfarin as a Probe*.
Journal of Pharmacology and Experimental Therapeutics, vol. 267, No. 2, Nov. 1993, pp. 1012–1016, XP000613057, S. Imaoka et al., *Identification of CYP2C23 Expressed In Rat Kidney as an Arachidonic Acid Epoxygenase*.
Romkes et al., Cloning and expression of complementary DNAs for multiple members of the human cytochrome P450IIC subfamily, Biochemistry, vol. 30, pp. 3247–3255.

*Primary Examiner*—John L. LeGuyader
*Assistant Examiner*—Andrew Wang
*Attorney, Agent, or Firm*—Birch, Stewart, Kolasch & Birch, LLP

[57] ABSTRACT

An oligonucleotide which can hybridize with a human-derived cytochrome P450IIC18 gene, one of the enzymes participating in the metabolic decomposition of medicines, has a GC content of 40–70%, and comprises 8 to 500 nucleotide units. The use of the oligonucleotide in the recognition or amplification of a DNA having the base sequence of this gene enables the presence or absence of mutation to be readily diagnosed and analyzed before the administration of a medicine. Thus it becomes possible to determine a safe dose of a medicine which has been difficult to use because of the occurrence of individual difference in drug-metabolizing ability and to use also a medicine which takes an active form by the action of this enzyme according to individuals.

24 Claims, 3 Drawing Sheets

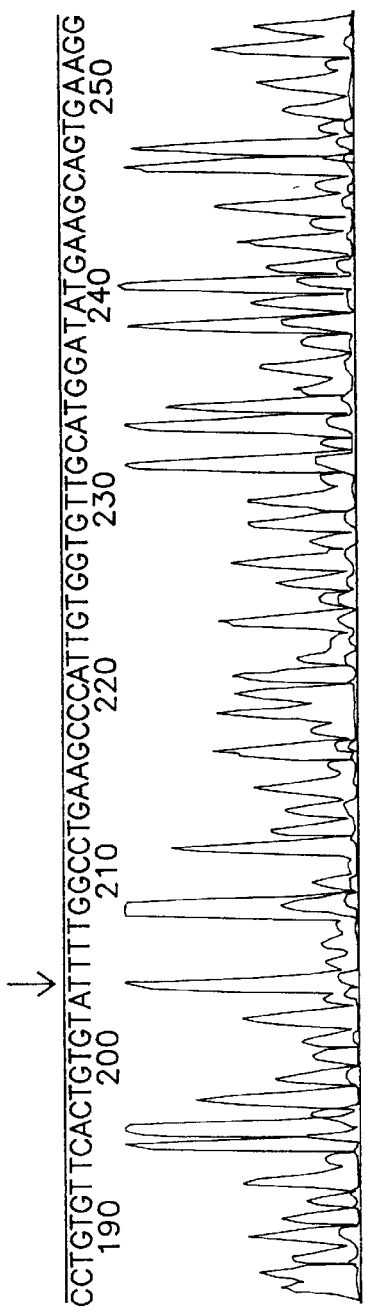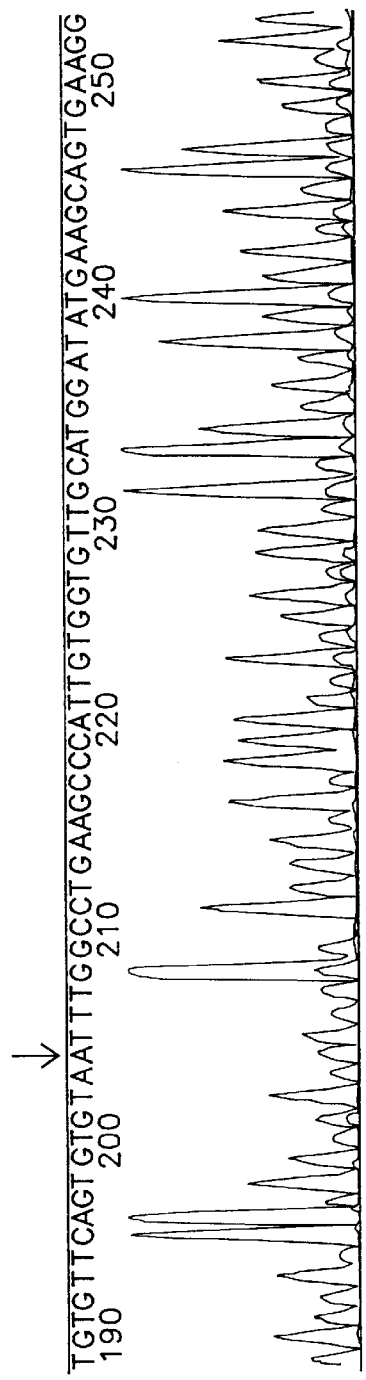
FIG. 3A Normal wild-type
FIG. 3B Mutant

OLIGONUCLEOTIDE FOR USE IN CHECKING PRESENCE OR ABSENCE OF MUTATION IN HUMAN-DERIVED CYTOCHROME P450IIC18 GENE

TECHNICAL FIELD

The present invention relates to an oligonucleotide for checking the presence or absence of mutation in a human-derived cytochrome P450IIC18 gene which is one of the enzymes participating in the metabolic decomposition of medicines. More particularly, the present invention relates to an oligonucleotide which is used to recognize or amplify a DNA having the base sequence of the gene and which is useful for diagnosing and analyzing the presence or absence of mutation before the administration of a medicine.

BACKGROUND ART

Cytochrome P450 is one of the metabolizing enzymes, in liver, participating in the metabolic decomposition of a variety of medicines. It has many molecular species and about twenty kinds of species are confirmed now in human beings. Among these molecular species, human-derived cytochrome P450IIC18 has been extensively studied on its ability to in vivo metabolize medicines (for example, tricyclic antidepressants such as amitriptyline, imipramine and the like, antiepileptics such as S-mephenytoin, ethotoin and the like, proton pump inhibitors such as omeprazole and the like, benzodiazepine preparations which are minor tranquilizers such as diazepam and the like, β-blocking agents such as propranolol and the like, and sleep inducing barbiturates such as hexobarbital and the like). However, individual differences in actual drug reaction and the like could not be explained. This is due to the presence of genetic polymorphism caused by mutation in human-derived cytochrome P450IIC18 and the relationship between this genetic polymorphism and the individual differences in drug reaction was not understood.

By the way, if the relationship between genetic polymorphism and individual differences in drug reaction is revealed, it becomes possible to easily predict the manifestation of the side effects and the conversion into an active form metabolite. That is, if the cause of genetic polymorphism (for example, mutation in a gene) in the enzymes (the enzyme means human-derived cytochrome P450IIC18 in the present invention) participating in the metabolic decomposition of medicines is revealed, it becomes possible to determine a safe dose of a medicine which has been difficult to use because of the occurrence of individual differences in drug-metabolizing function, by means of diagnosing and analyzing the presence or absence of mutation in such the gene before the administration of a medicine. It also becomes possible to use a medicine which takes an active form by the action of the enzyme according to individuals.

For this reason, there is a problem that, in order to clarify the relationship between genetic polymorphism of the enzymes participating in the metabolic decomposition of medicines and individual differences in drug reaction, when that genetic polymorphism is caused by mutation in a gene of the enzymes, what kind of mutation can be used and how the presence or absence of mutation in the gene can be diagnosed and analyzed before the administration of a medicine.

DISCLOSURE OF THE INVENTION

In view of the above situation, the present inventors studied hard to clarify the relationship between genetic polymorphism of the enzymes participating in the metabolic decomposition of medicines and individual differences in drug reaction. As the result, the present inventors have discovered that the relationship between genetic polymorphism of a specific enzyme and individual differences in drug reaction is based on mutation in the enzyme gene and that the presence or absence of mutation in such a gene can be checked by hybridization analysis of the base sequence including that of the mutated site or by the presence or absence of the action of a restriction enzyme which recognizes the base sequence of the mutated site. And the present inventors found out an oligonucleotide for recognizing or amplifying a DNA having a mutated site in the specific enzyme gene upon above checking, that is, an oligonucleotide for diagnosing and analyzing the presence or absence of mutation in the specific enzyme gene before the administration of a medicine, which resulted in completion of the present invention.

That is, the present invention provides an oligonucleotide (hereinafter referred to as "present oligonucleotide") for checking the presence or absence of mutation in a human-derived cytochrome P4501IC18 gene which comprises 8 to 500 nucleotides, wherein a GC content (hereinafter "GC content" means a ratio of the total number of nucleotides G and C relative to the total number of nucleotides of the oligonucleotide) is 40% to 70%, and wherein said oligonucleotide can hybridize with the gene.

BRIEF DESCRIPTION OF DRAWINGS

FIG. 3 is a view showing the results of base sequence analysis of an exon 2 area in a human-derived cytochrome P450IIC18 gene. To is seen that there is a sample including a gene having a mutation where T at base number 204 is replaced by A, in the base sequence of an exon 2 area in a human-derived cytochrome P450IIC18 gene. This means a codon change from TAT to TAA, that is, mutation from 69th tyrosine in the amino acid sequence to a termination codon.

DETAILED DESCRIPTION OF THE INVENTION

Figure 1:
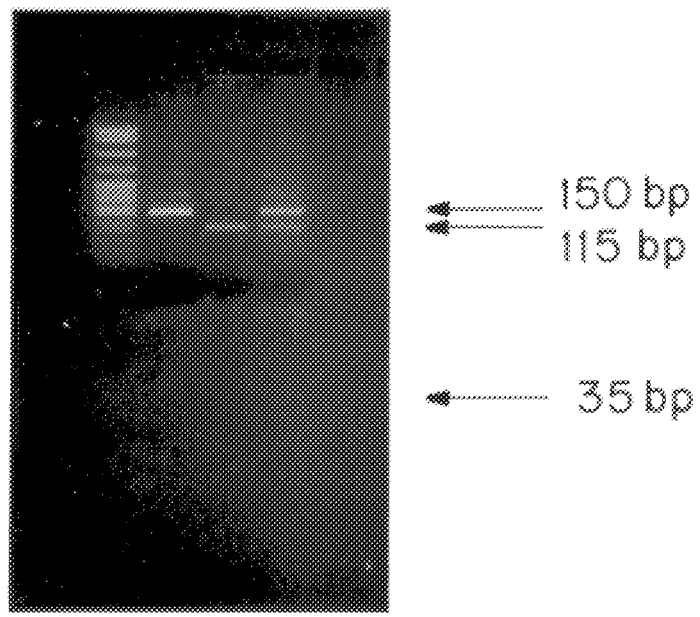
FIG. 1 is a view showing the results of a test where, with respect to genomic DNA extracted from a specimen of human cell tissue, a part of the DNA (150 bp area) having the base sequence of a mutant gene of human-derived cytochrome P450IIC18 was amplified, digested with a restriction enzyme which recognizes the base sequence of the mutant gene, and the resulting DNA fragments were subjected to electrophoresis analysis. It is seen that there are various types of samples including DNA's having the base sequence of a normal wild-type gene and/or mutant gene of human-derived cytochrome P450IIC18. Lane M represents molecular weight marker (product from pBR322 digested with Msp I). Lane A represents a homogenous sample containing a single normal wild-type gene. Lane B represents a homogenous sample containing a single mutant gene. Lane C represents a heterologous sample containing a normal wild-type gene and a mutant gene.

The present oligonucleotide is not limited to a specified one, as long as it can hybridize with a human-derived cytochrome P450IIC18 gene, its GC content is 40% to 70% and it comprises 8 to 500 nucleotides. A preferable example thereof is a mutant gene of human-derived cytochrome P450IIC18 that has mutation at least at base number 204 in an exon 2 area in a normal wild-type gene of the same, and the mutated site is contained in a recognition or amplification region of the oligonucleotide. Of course, the present oligonucleotide may or may not have the base sequence of the mutated site. In addition, the present oligonucleotide should be labelled with a radioactive or non-radioactive substance when used for recognizing a DNA having the base sequence of the above mutant type gene.

The GC content in the present oligonucleotide is generally 40% to 70%, preferably 40% to 60%, more preferably 40% to 50%. The number of nucleotides in the present oligonucleotide is generally 8 to 500 and, when used for recognizing a DNA, preferably 8 to 100, more preferably 15 to 50 and, when used for amplifying a DNA, preferably 15 to 30, more preferably 20 to 30.

Embodiments of the present oligonucleotide are illustrated below but are not limited thereto.

(1) 5'-TTCTCAAAAGTCTATGGC-3' (corresponding to SEQ ID No. 1)
(2) 5'-AACTTTTTCAGCCACTGG-3' (corresponding to SEQ ID No. 2)
(3) 5'=TTCAAGCCTGTTTTCCATCC-3' (corresponding to SEQ ID No. 3)
(4) 5'-GCAGAACAGAAAACAGAAGC-3' (corresponding to SEQ ID No. 4)
(5) 5'-TCCTCGATGCTCCCTCTTCC-3' (corresponding to SEQ ID No. 5)
(6) 5'-TGCAGGGAGCACAGCCCAGG-3' (corresponding to SEQ ID No. 6)
(7) 5'-AGTCACCCACCATTGGTTTT-3' (corresponding to SEQ ID No. 7)
(8) 5'-TGATCAATCAGGGCC-3' (corresponding to SEQ ID No 8)
(9) 5'-GCCCAGTACATACACATGTACACATAC-ACACGATA-3' (corresponding to SEQ ID No. 9)
(10) 5'-CTGTGTAATTTGGCCTG-3' (corresponding to SEQ ID No. 10)
(11) Oligonucleotide which is a DNA fragment of a mutant gene corresponding to the base sequence of base number 169 to 218 in an exon 2 area in a normal wild-type gene of human-derived cytochrome P450IIC18 (50 bp) (corresponding to SEQ ID No. 11)
(12) Oligonucleotide which is a DNA fragment of a mutant gene corresponding to the base sequence of base number 169 to 268 in an exon 2 area in a normal wild-type gene of human-derived cytochrome P450IIC18 (100 bp) (corresponding to SEQ ID No. 12)
(13) Oligonucleotide which is a DNA fragment composed of a mutant gene corresponding to the base sequence of base number 169 to 331 in an exon 2 area in a normal wild-type gene of human-derived cytochrome P450IIC18 and a mutant gene corresponding to the sequence of the first to 37th bases in an intron 2 area in the same normal wild-type gene (200 bp) (corresponding to SEQ ID No. 13)
(14) Oligonucleotide which is a DNA fragment composed of a mutant gene corresponding to the base sequence of base number 169 to 331 in an exon 2 area in a normal wild-type gene of human-derived cytochrome P450IIC18, a mutant gene corresponding to the sequence of the first to 191st bases in an intron 2 area in the same normal wild-type gene, a mutant gene corresponding to the base sequence of base number 332 to 481 in an exon 3 area in the same normal wild-type gene, and the base sequence GTGGGT-GACT (513 bp).

Among the above embodiments, oligonucleotides (1) to (9) are useful as a primer for DNA amplification in polymerase chain reaction (PCR) method, and oligonucleotides (10) to (14) are useful as a probe for DNA recognition in hybridization analysis.

When a PCR method is carried out using the above present oligonucleotide as a primer, a combination of two kinds of primers for forward and reverse amplification is generally used. For example, when a combination of the oligonucleotide shown in SEQ ID 1 and that shown in SEQ ID 2 is used, the chain length of genomic DNA to be amplified (hereinafter referred to as "amplification chain length") is 150 bp. Likewise, the amplification chain length is 250 bp in the case of a combination of the oligonucleotide shown in SEQ ID 1 and that shown in SEQ ID 3, 350 bp in the case of a combination of the oligonucleotide shown in SEQ ID 1 and that shown in SEQ ID 41 450 bp in the case of a combination of the oligonucleotide shown in SEQ ID 1 and that shown in SEQ ID 5, 550 bp in the case of a combination of the oligonucleotide shown in SEQ ID 1 and that shown in SEQ ID 6, 614 bp in the case of a combination of the oligonucleotide shown in SEQ ID 1 and that shown in SEQ ID 7, 102 bp in the case of a combination of the oligonucleotide shown in SEQ ID 1 and that shown in SEQ ID 8, and 222 bp in the case of a combination of the oligonucleotide shown in SEQ ID 1 and that shown in SEQ ID 9.

When the present oligonucleotide has not more than about 100 nucleotides, it can be generally prepared with a commercially available automated DNA synthesizer using β-cyanoethylphosphoramidite method or thiophosphite method. On the other hand, when the present oligonucleotides have not less than about 100 nucleotides, it can be obtained by a conventional method such as treatment of a mutant gene of human-derived cytochrome P450IIC16 with a restriction enzyme or cloning of the same gene.

The present oligonucleotide is useful for diagnosing and analyzing, before the administration of a medicine, the presence or absence of mutation in a human-derived cytochrome P450IIC18 gene contained in a specimen. That is, it becomes possible to check the presence or absence of mutation by hybridization analysis using the present oligonucleotide labelled with a radioactive or non-radioactive substance as a probe with respect to genomic DNA prepared from hair, peripheral blood, oral cavity epithelial cells and the like, and subsequent direct visual determination, or by amplification of the genomic DNA by a PCR method using the present oligonucleotide as a primer, and subsequent indirect determination by the presence or absence of mutation by action of a restriction enzyme which recognizes the base sequence of a mutated site. For that reason, the examination of individual differences in the enzyme's ability to metabolize a medicine becomes unnecessary by administering to a subject a medicine which is specifically metabolized by human-derived cytochrome P450IIC18 after careful examination of its dose, then measuring an amount of a metabolite by sophisticated techniques and complicated procedures, which leads to higher speed, higher efficiency, higher precision and lower cost in a test.

Genomic DNA contained in a specimen can be prepared from any cell tissues from which genomic DNA can be collected, such as hair, peripheral blood, oral cavity epithelial cells and the like, by conventional methods (see, for example, Masahiro MATSUMURA, "Labo-Manual Genetic Engineering", Maruzen (1988) and TAKARA PCR Technical News No. 2, TAKARA SHUZO (1991.9)).

For example, in the case of hair, two or three hairs are washed successively with sterile water and ethanol and chopped into pieces having lengths of 2–3 mm. 200 μl of a BCL buffer (10 mM Tris-HCl (pH 7.5), 5 mM $MgCl_2$, 0.32M sucrose, 1% Triton X-100) is added thereto, and proteinase K and SDS are added to a final concentration of 100 μ/ml and 0.5% (w/v), respectively, followed by mixing. This mixture is treated at 70° C. for one hour, followed by extraction with phenol/chloroform to obtain genomic DNA.

In the case of peripheral blood, genomic DNA is obtained by extraction from a 10 ml blood sample using a DNA extraction kit (manufactured by STRATAGENE).

In the case of oral cavity epithelial cells, an inside part of bucca is scraped with a spatula or the like to collect a small amount of oral cavity epithelial cells. To the resulting sample is added a cooled TNM solution (20 mM Tris-HCl (pH 7.5), 0.1M NaCl, 1.5 mM $MgCl_2$), followed by homogenization at the temperature of ice and centrifugation (2000 rpm, 5 min., 4° C.). The resulting pellet is rinsed slightly with a small amount of a cooled TNE solution (10 mM Tris-HCl (pH 7.5), 0.1M NaCl, 1 mM EDTA) and a fresh TNE solution is added thereto, followed by stirring at the temperature of ice. After suspension, proteinase K and SDS are added thereto to a final concentration of 100 μg/ml and 0.3% (w/v), respectively, followed by mixing. This mixture is treated at 60° C. for 4 hours to overnight, followed by extraction with phenol/chloroform to obtain genomic DNA.

The genomic DNA thus prepared is amplified, if necessary, by a PCR method (Saiki et al., Science, 230, 1350–1354 (1985); Williams et al., Nucleic Acids Research, 18, 22, 6531–6535 (1991)), and subjected to hybridization analysis using the present oligonucleotide as a probe after separation by electrophoresis method or without separation whereby the presence or absence of mutation in a human-derived cytochrome P450IIC18 gene can be visually determined directly. As an example of hybridization analysis, there is a conventional point mutation detection method, for example, dot blot hybridization method, RFLP (Restriction Fragment Length Polymorphism) method and the like using the present oligonucleotide as a probe. A PCR method is explained in detail below.

When the present oligonucleotide is used as a probe for hybridization analysis, it is necessary to label it with a radioactive or non-radioactive substance by random priming method (Anal. Biochem., 132, 6 (1983)), nick translation method (J. Mol. Biol., 113, 237 (1977)) or the like. Examples of such labelled oligonucleotides are a radioactive probe labelled by incorporating therein a radioactive nucleotide such as [$\alpha^{32}$P] dCTP and the like by nick translation method, a non-radioactive probe labelled by incorporating therein a biotinylated nucleotide such as biotin-11-dUTP, biotin-14-dATP and the like by a random priming method or nick translation method, and a non-radioactive probe labelled by cross-linking an enzyme such as alkaline phosphatase, peroxidase and the like to the base site using glutaraldehyde.

Representative methods used for hybridization analysis are explained in detail below.

Dot blot hybridization is carried out, for example, according to the following steps: a) genomic DNA is prepared from a specimen as described above; b) if necessary, amplification is carried out using the prepared genomic DNA as a template so as to include at least a mutated site of a human-derived cytochrome P450IIC18 gene in a region to be amplified; c) the (amplified) genomic DNA is hybridized by 1) thermally denaturing at 90° to 100° C. for 3 to 5 minutes to form single strands, then spotting this genomic DNA on a nylon filter (Hybond N, manufactured by AMERSHAM), drying it on a filter paper and then irradiating with ultraviolet rays to fix, and 2) incubating the resulting DNA-fixed filter and the above-described probe, that is, the present oligonucleotide labelled with a radioactive or non-radioactive substance, for example, at 40° to 50° C. for 10 to 20 hours and, thereafter, a probe which has hybridized is detected by various methods. When a radioactive probe labelled with $^{32}$P or the like is used, an X-ray film is exposed to the light from the probe, to detect a signal. When a non-radioactive probe labelled with a biotinylated nucleotide is used, the present oligonucleotide is labelled with an enzyme of biotinylated alkaline phosphatase via streptavidin, nitroblue tetrazolium as a substrate and 5-bromo-4-chloro-3-indolyl-phosphoric acid are added thereto, and an X-ray film is exposed to the light from color development or emission caused by a reaction between an enzyme and a substrate to detect a signal. When a non-radioactive probe labelled with an enzyme such as alkaline phosphatase, peroxidase and the like is used, 4-methoxy-4-(3-phosphatophenyl)spiro[1,2-dioxyethane-3, 2-adamantane] (PPD) or the like is used as a substrate in the former case, and luminol or the like is used in the latter case and an X-ray film is exposed to the light from color development or emission caused by a reaction between an enzyme and a substrate to detect a signal.

RFLP method is carried out, for example, according to the following steps: a) genomic DNA is prepared from a specimen as described above; b) if necessary, amplification is carried out using the prepared genomic DNA as a template so as to include at least a mutated site of a human-derived cytochrome P450IIC18 gene in a region to be amplified; c) the (amplified) genomic DNA is completely digested using a restriction enzyme which recognizes the base sequence of a mutated site of the gene (for example, . . . AATT . . . as positive recognition, and . . . ATTT . . . as negative recognition); d) the restriction enzyme-treated genomic DNA is subjected to agarose gel electrophoresis (electrophoresis is preferably carried out overnight at low voltage around 20 V) (when genomic DNA is amplified in step b), this step can be omitted); e) the restriction enzyme-treated genomic DNA (separated by electrophoresis) is transferred by capillary method or electrically from the above agarose gel to a nylon filter or nitrocellulose filter to obtain a blot membrane; f) the restriction enzyme-treated genomic DNA on the blot membrane is hybridized by 1) thermally denaturing at 90° to 100° C. for 3 to 5 minutes to form single strands, drying it, then irradiating with ultraviolet rays to fix, and 2) incubating the resulting DNA-fixed filter and the above probe, that is, the present oligonucleotide labelled with a radioactive or non-radioactive substance, for example, at 40° to 50° C. for 10 to 20 hours and, thereafter, a probe which has hybridized is detected by various methods. When a radioactive probe labelled with $^{32}$P or the like is used, an X-ray film is exposed to the light from the probe to detect a signal. When a non-radioactive probe labelled with biotinylated nucleotide is used, the present oligonucleotide is labelled with an enzyme of biotinylated alkaline phosphatase via streptavidin, nitroblue tetrazolium as a substrate and 5-bromo-4-chloro-3-indolyl-phosphoric acid are added thereto, and an X-ray film is exposed to the light from color development or emission caused by a reaction between an enzyme and a substrate to detect a signal. When a non-radioactive probe labelled with an enzyme such as alkaline phosphatase, peroxidase and the like is used, 4-methoxy-4-(3-phosphatophenyl)spiro[1,2-dioxyethane-3,2-adamantane] (PPD) or the like is used as a substrate in the former case, and luminol or the like is used in the latter case and an X-ray film is exposed to the light from color development or emission caused by a reaction between an enzyme and a substrate to detect a signal.

In addition, a DNA having the base sequence of a mutant gene among human-derived cytochrome P450IIC18 genes present in the genomic DNA prepared as described above is amplified by a PCR method using the present oligonucleotide as a primer and the presence or absence of cleavage by a restriction enzyme which recognizes the base sequence of a mutated site is examined and, thereby, the presence or absence of a mutation in a human-derived cytochrome P450IIC18 gene can be checked indirectly.

A PCR method is a method by which amplification is carried out by repeating a DNA replicating cycle comprising a denaturating step, a primer annealing step and an extension step by a DNA polymerase.

The PCR method is carried out, for example, by repeating DNA replicating cycle about 20 to about 50 times, preferably about 25 to about 40 times in an amplification buffer, to which the present oligonucleotide, a DNA polymerase, four kinds of bases (dATP, dTTP, dCTP and dGTP) and genomic DNA have been added previously, and which contains about 1.0 mM to about 4.0 mM, preferably about 1.5 mM to about 3.0 mM magnesium chloride or the like. As a primer, the present oligonucleotide can be used alone or in combination thereof. Generally, it is preferable that a PCR reaction is carried out with two kinds of primers, forward and reverse.

Each step in the PCR method can be carried out, for example, under the following conditions.

The denaturing step is carried out, for example, by heating at about 90° to about 95° C., for about 94° C. to about 95° C. for about 1 minute to about 3 minutes, preferably for about 1 minute to about 2 minutes. The primer annealing step is carried out, for example, by incubation with a primer at about 30° C. to about 55° C., preferably about 37° C. to about 50° C. for about 3 seconds to about 3 minutes, preferably for about 5 seconds to about 1 minute. The extension step by a DNA polymerase is carried out, for example, by treatment with a heat-resistant DNA polymerase at about 70° C. to about 78° C., preferably about 72° C. to about 75° C. for about 15 seconds to about 4 minutes, preferably for about 30 seconds to about 5 minutes. As the heat-resistant DNA polymerase, commercially available heat-resistant DNA polymerases such as that manufactured by T-KARA SHUZO K.K. and the like can be used.

A restriction enzyme which recognizes the base sequence of a mutant gene (example thereof is a restriction enzyme which has a recognition site of the base sequence . . . AATT . . . and digests a DNA at this site, for example, the commercially available restriction enzymes such as TspEI (Tsp509I) and the like) is reacted with a DNA having the base sequence of the mutant gene of the human-derived cytochrome P450IIC18 amplified by the above method to, digest the amplified DNA at the recognition site. Then, the restriction enzyme-treated DNA's are separated by an electrophoresis method normally used in conventional DNA separation. Generally, an about 3% to about 20% polyacrylamide gel, an about 2% to about 6% agarose gel or the like for shorter fragments, is used for separating short DNA fragments of not larger than 1000 bp, and an about 0.2% to about 2% agarose gel or the like is used for separating long DNA fragments of not smaller than 1000 bp.

As a buffer used for electrophoresis, there are Tris-phosphate buffer (pH 7.5–8.0), Tris-acetate buffer (pH 7.5–8.0), Tris-borate buffer (pH 7.5–8.3) and the like. In particular, Tris-acetate buffer is preferable. In addition, EDTA can be added to such buffers, if necessary.

Examples of electrophoresis conditions are 150V for 20 minutes, 100V for 40 minutes, 50V for 80 minutes and the like.

Examples of a size marker are a size marker obtained by completely hydrolyzing a plasmid pBR322 with a restriction enzyme MspI, a size marker obtained by completely hydrolyzing a A phage DNA with a restriction enzyme Hind III and the like. Commercially available size markers manufactured by NIPPON GENE K.K. or TAKARA SHUZO K.K. can be used.

As a visual detection method after an amplified DNA having the base sequence of a mutant gene of human-derived cytochrome P450IIC18 has been treated with a restriction enzyme, there is a method for detecting a DNA by a staining method using a substance, such as ethidium bromide and the like, which is a phenanthridine pigment which interacts with nucleic acid.

In this staining method, when a substance such as ethidium bromide and the like is previously added to a buffer used in electrophoresis to a final concentration of about 0.5 $\mu$l/ml, a red band of a DNA bound with ethidium bromide can be detected even during the electrophoresis run by irradiating the gel with ultraviolet rays having a wavelength of 254 nm or 366 nm in the dark. However, a red band of a DNA bound with ethidium bromide is normally detected by dipping the gel in a solution of a substance such as ethidium bromide and the like for about 15 minutes to about 60 minutes after the run and then irradiating the gel with ultraviolet rays having a wavelength length of 254 nm or 366 nm in the dark.

As the result, it becomes possible to diagnose and analyze the presence or absence of mutation in a human-derived cytochrome P450IIC18 gene before the administration of a medicine by determining whether or not a detected amplified DNA has been produced by digestion with a restriction enzyme which recognizes the base sequence of a mutated site (determination becomes easy by, for example, simultaneously carrying out a test using as a control an authentic gene which has been predetermined to be normal wild-type or mutant, and determination can also be made from the molecular weight or the number of an amplified DNA to be detected). If necessary, more precise diagnosis and analysis can be carried out by combining the respective results obtained by separately using various present oligonucleotides. In addition, the precision of diagnosis and analysis can be further improved by investigating whether the same behavior is shown or not when varying the conditions in PCR method such as a temperature in the primer annealing step, the concentration of magnesium in a buffer for reaction and the like.

In the above-described method, a DNA having the base sequence of a mutant gene of human-derived cytochrome P450IIC18 is amplified, digested with a restriction enzyme which recognizes the base sequence of the mutant gene and the resulting DNA fragments are analyzed by electrophoresis. Alternatively, other methods utilizing PCR, for example, Allele-specific PCR method (Nature, 324, 163 (1986)), PCR-direct sequencing method (Proc. Natl. Acad. Sci. U.S.A., 85, 7652 (1988)), PCR-SSCP (PCR-Single Strand Conformation Polymorphism) method (Hum. Mutation, 2, 338 (1989)), LCR (Ligase Chain Reaction) method (Genomics, 4, 560 (1989)) and the like can be used. Of course, the present oligonucleotide can be used in any method having a step for amplifying a DNA having the base sequence of a mutant gene of human-derived cytochrome P450IIC18.

The following Examples illustrate the present invention in more detail but the scope of the present invention is not limited to these Examples.

EXAMPLE 1
Preparation of oligonucleotides used as primers for PCR method

With respect to a mutant gene having a mutation at base number 204 in an exon 2 area in a human-derived cytochrome P450IIC18 gene, two oligonucleotides comprising 18 nucleotides, having a base sequence that spans the mutated site in the region to be amplified and having a GC content of about 40% were designed. Based on the designed base sequences, two kinds of oligonucleotides shown by SEQ ID Nos. 1 and 2 were prepared using an automated DNA synthesizer (Model 394, manufactured by APPLIED BIOSYSTEMS).

The base sequence of a normal wild-type gene of human-derived cytochrome P450IIC18 is described in, for example, Mol. Pharmacol., 40, 375 (1991) and the base sequence of a mutant gene is explained in Reference Example 3 below.

EXAMPLE 2
Preparation of oligonucleotide used as probe for hybridization analysis With respect to the same mutant gene as described in Example 1, an oligonucleotide comprising 17 nucleotides, having such the base sequence that includes the mutated site in the region to be recognized and having a GC content of about 53% was designed. Based on the designed base sequence, an oligonucleotide shown by SEQ ID No. 10 was prepared using an automated DNA synthesizer (Model 394, manufactured by Applied Biosystems). Then, fluorescein was cross-linked to the base site of this oligonucleotide using commercially available ECL-random prime DNA labelling detection system (manufactured by AMERSHAM) to obtain a labelled non-radioactive probe.

Reference Example 1
Extraction of genomic DNA contained in specimen (hair)

Hair was used as cell tissue from which genomic DNA can be collected. Two or three hairs were washed with sterile water and further washed with 100% ethanol. The hairs were air dried at room temperature and chopped into pieces having lengths of 2–3 mm, which were transferred to a plastic tube. 200 μl of a BCL buffer (10 mM Tris-HCl (pH 7.5), 5 mM MgCl$_2$, 0.32M sucrose, 1% Triton X-100) was added thereto, followed by stirring. After complete suspension, 1 μl of a 20 mg/ml proteinase K (manufactured by Boehringer Mannheim) solution (final concentration of 100 μg/ml) and 10 μl of a 10% SDS solution (final concentration of 0.5% (w/v)) were successively added thereto in small portions and mixed while mildly shaking. After this mixture was incubated at 70° C. for 1 hour, an equal amount of phenol was added thereto, followed by vigorous shaking and centrifugation (3000 rpm, 10 min., 4° C.). The aqueous layer was recovered with a pipette having a large opening so as not to disturb the phenol layer, followed by another phenol extraction. An equal amount of chloroform was added to the recovered aqueous layer, the mixture was shaken vigorously and centrifuged (3000 rpm, 5 min., 4° C.) to recover the aqueous layer. To this was added 500 μl of 100% ethanol, the mixture was incubated at −80° C. for 20 minutes and centrifuged (3000 rpm, 10 min., 4° C.). The resulting pellet was dried to solidify and dissolved in 50 μl of a TE solution (10 mM Tris-HCl (pH 7.5), 1 mM EDTA). The resulting genomic DNA solution (10 pg of DNA) was transferred to a plastic tube and stored at 4° C. until use for test.

Reference Example 2
Extraction of genomic DNA contained in a specimen (peripheral blood)

Peripheral blood was used as cell tissue from which genomic DNA can be collected. 10 ml of blood was collected and genomic DNA was extracted from the resulting blood using a DNA extraction kit (manufactured by STRATAGENE). The resulting genomic DNA solution (250 μg of DNA) was transferred to a plastic tube and stored at 4° C. until use for test.

EXAMPLE 3
Genetic diagnostic method I using present oligonucleotide

PCR was carried out in a 10 mM Tris-HCl buffer (pH 8.3), to which 100 picomoles each of an oligonucleotide (for forward) shown by SEQ ID No. 1 and an oligonucleotide (for reverse) shown by SEQ ID No. 2 (described in Example 1), 2.5 units of a thermo-stable DNA polymerase (pfu DNA polymerase, manufactured by STRATAGENE), 1.0 nanomole each of four kinds of bases (dATP, dTTP, dCTP and dGTP) and 0.02 μg of the genomic DNA obtained in Reference Example 1 had been previously added, and which contained 0.01% (w/v) gelatin, 50 mM potassium chloride and 2.5 mM magnesium chloride. About 20 μl of a mineral oil was added to 100 μl of the reaction solution to prevent evaporation of the reaction solution. Each step of the above PCR method was carried out under the following conditions.

The first cycle was carried out once by heating at 94° C. for 2 minutes in the denaturing step and incubating with a primer at 50° C. for 5 minutes in the primer annealing step. Thereafter, the second cycle was carried out 34 times by heating at 94° C. for 1 minute in the denaturing step, incubating with a primer at 50° C. for 5 seconds in the primer annealing step and treating with a thermo-stable DNA polymerase at 75° C. for 2 minutes and 30 seconds in the extension step by a DNA polymerase. Further, the third cycle was carried out once by heating at 95° C. for 1 minute in the denaturing step, incubating with a primer at 50° C. for 5 seconds in the primer annealing step and treating with a thermo-stable DNA polymerase at 75° C. for 5 minutes in the extension step by a DNA polymerase.

Then, the resulting amplified genomic DNA was digested (65° C., 1 hour) with a restriction enzyme TspE1 (Tsp509I) (manufactured by NEW ENGLAND BIOLABS) to obtained a digested amplified genomic DNA. This digested amplified genomic DNA was separated by electrophoresis at 150V for 20 minutes in a 40 mM Tris-20 mM acetate buffer (pH 8.0) containing 1 mM EDTA using a 4% agarose gel for short fragments (manufactured by FMC). Upon separation, a plasmid pBR322 which had been completely hydrolyzed with a restriction enzyme MspI (manufactured by NIPPON GENE) was used as a size marker. After completion of separation, the gel was dipped in a 0.5 μg/ml aqueous solution of ethidium bromide for 30 minutes and irradiated with ultraviolet rays having a wavelength of 254 nm in the dark to detect a red band of a DNA associated with ethidium bromide. The results thereof are shown in FIG. 1.

When a sample was prepared from a specimen having only a mutant gene among specimens having mutation in a human-derived cytochrome P450IIC18 gene, two amplified genomic DNA's of about 115 bp and about 35 bp were detected. On the other hand, when a sample was prepared from a heterologous specimen having a mutant and a normal wild-type gene, three amplified genomic DNA's of about 150 bp, about 115 bp and about 35 bp were detected. Further, when a sample was prepared from a specimen having no mutation in a human-derived cytochrome P450IIC18 gene (that is, a homogenous sample was prepared from a specimen having only a normal wild-type gene), only about 150 bp amplified genomic DNA was detected.

EXAMPLE 4
Genetic diagnostic method II using present oligonucleotide

5 μg of the genomic DNA obtained in Reference Example 2 was completely digested at 65° C. for 16 hours using a restriction enzyme TspEI (Tsp509I) (manufactured by NEW ENGLAND BIOLABS). The resulting restriction enzyme-treated genomic DNA was separated by 0.8% agarose gel electrophoresis (20V, 16 hours). The restriction enzyme-treated genomic DNA which had been separated by electrophoresis was transferred from the agarose gel to a nylon filter (Hybond-N, manufactured by AMERSHAM) using a capillary type alkali blotting method (Hybond Blotting Membrane Manual, AMERSHAM) described in Nuc. Acids Res., 3, 7207 (1985) and the like to obtain a blot membrane. The blotting time was 2 hours. The blot membrane thus obtained was rinsed slightly with a 2×SSC buffer (0.3M NaCl, 0.03M sodium citrate, pH 7.0), heat-treated at 80° C. for 10 minutes, air dried on a filter paper for 20 minutes, and irradiated with ultraviolet rays for 2 minutes to fix the restriction enzyme-treated genomic DNA to a blot membrane. Then, 1 ml of a hybridization buffer containing 0.5M sodium chloride per 4 cm² of the resulting DNA-fixed filter was placed in Hybridization Bag, which was thermally sealed and pre-hybridized at 42° C. for 1 hour. Thereafter, replacement with an equal amount of a hybridization buffer was carried out, the probe prepared in Example 2, that is, the present oligonucleotide labelled with fluorescein was added at a ratio of 10 ng/ml, and the DNA-fixed filter was incubated at 60° C. for about 16 hours while mildly shaking to form a DNA-DNA hybrid.

After the reaction was completed, the DNA-fixed filter was washed at 42° C. for 10 minutes using 2 ml of a 0.5×SSC (7.5 mM sodium citrate, 75 mM NaCl, pH 7.0) washing solution containing 6M urea and 0.4 % by weight of SDS per 1 cm² of the filter. The filter was further washed for 10 minutes then 20 minutes while replacing the washing solution each time. Further, the filter was washed at room temperature for 5 minutes using a 0.03M sodium citrate (pH 7.0) washing solution, containing 0.3M NaCl, in the same amount as that described above. This washing was repeated once and the DNA-fixed filter was allowed to stand on a filter paper for 1 minute. After fixation of the filter, addition reaction of anti-fluorescein antibody and washing procedures, the filter was dipped in a mixed solution of detection reagents (ECL direct labelling kit, manufactured by AMERSHAM) and shaken at room temperature for 1 minute to cause an emission reaction of the probe. An X-ray film was exposed to the light from this emission for 1 hour, and developed to detect a signal. As a size marker, a plasmid pBR322 which had been completely hydrolyzed with a restriction enzyme aspI (manufactured by NIPPON GENE) or a λ phage DNA which had been completely hydrolyzed with a restriction enzyme Hind III (manufactured by TAKARA SHUZO K.K.) was used.

Figure 2:
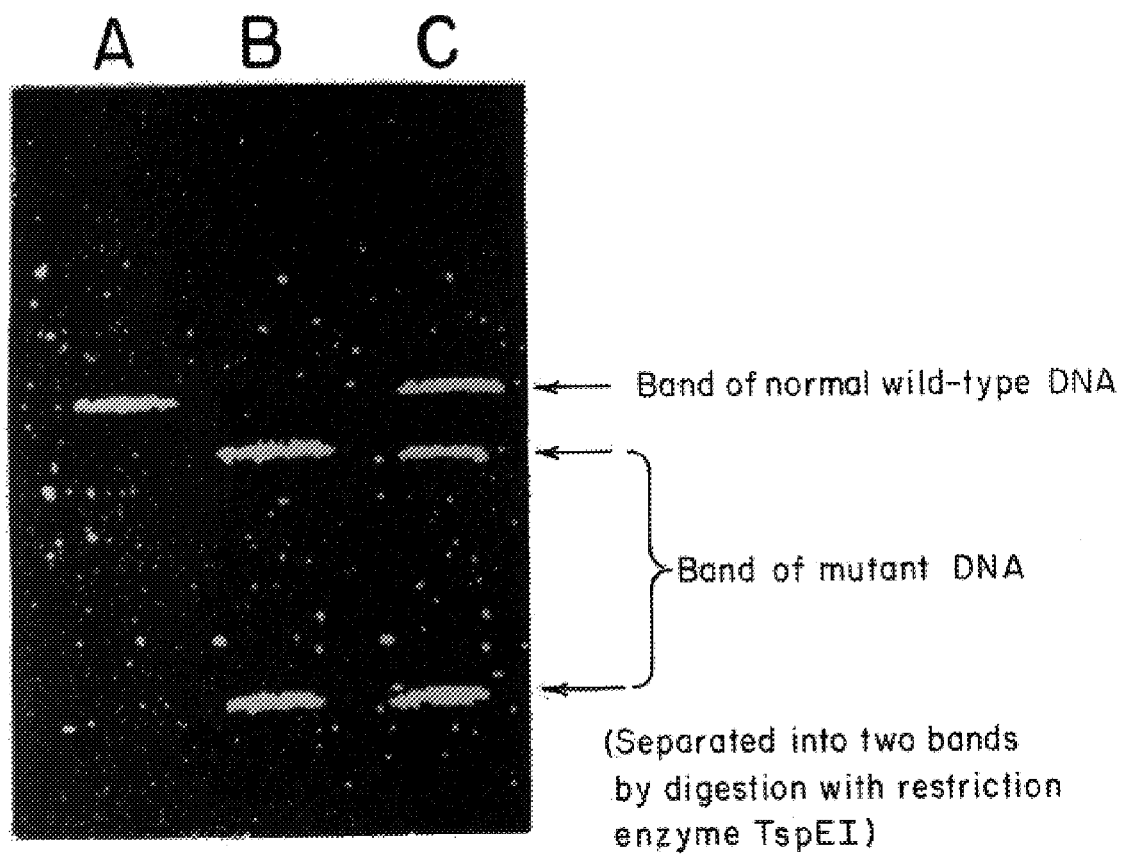
FIG. 2 is a view showing the results of a test where genomic DNA extracted from a specimen of human cell tissue was digested with a restriction enzyme which recognizes the base sequence of a mutant gene, the resulting DNA fragments were electrophoresed, and subjected to hybridization analysis using the present oligonucleotide as a probe. It is seen that there are various types of samples including DNA's having the base sequence of a normal wild-type gene and/or mutant gene of human-derived cytochrome P450IIC18. Lane A represents a homogenous sample containing a single normal wild-type gene. Lane B represents a homogenous sample containing a single mutant gene. Lane C represents a heterologous sample containing a normal wild-type gene and a mutant gene.

As the result, when a sample was prepared from a specimen having only a mutant gene among specimens having mutation in a human-derived cytochrome P450IIC18 gene, two bands corresponding to smaller molecular weight (small in DNA chain length) were detected. On the other hand, when a sample was prepared from a heterologous specimen having a mutant and a normal wild-type gene, three genomic DNA's were detected. Further, when a sample was prepared from a specimen having no mutation in a human-derived cytochrome P450IIC18 gene (that is, prepared from a homogenous specimen having only a normal wild-type gene), one band corresponding to larger molecular weight (large in DNA chain length) was detected. The results thereof are shown in FIG. 2.

Reference Example 3
Sequencing analysis of exon 2 area in human-derived cytochrome P450IIC18 gene The genomic DNA's obtained in Reference Examples 1 and 2 were amplified by a PCR method according to the method described in Example 3. The resulting amplified genomic DNA was ligated to a commercially available vector pUC118 (manufactured by TAKARA SHUZO K.K.) by a conventional method to construct a plasmid. The resulting plasmid was introduced into competent *Escherichia coli* HB-101 (manufactured by TAKARA SHUZO K.K.) to obtain a transformed clone. A plasmid DNA was prepared from 5 clones per sample by alkali rapid method (Nucleic Acids Res., 7, 1513 (1979)), and this was used as a template to determine the base sequence using a Taq Dye-dideoxy-terminator cycle sequencing kit (manufactured by APPLIED BIOSYSTEMS) and an automated DNA-Sequencer (model 373A, manufactured by APPLIED BIOSYSTEMS) [Fundamental principle: Dideoxy Chain Terminator Method (Science, 214, 1205 (1981))]. The base sequence was analyzed in both directions from 5' terminal to 3' terminal and from 3' terminal to 5' terminal to assure no misreading. As the result, it was found that, in both cases where peripheral blood or hair was used as cell tissue, there is a specimen containing a gene having mutation where T at base number 204 is replaced with A in the base sequence of an exon 2 area in a human-derived cytochrome P450IIC18 gene (see FIG. 3). This means a codon change from TAT to TAA, that is, mutation from 69th tyrosine in the amino acid sequence to a termination codon. This shows that, in human being having only this mutation, a human-derived cytochrome P450IIC18 gene can not be completely translated leading to the manifestation of abnormal expression of the gene. Further, since the base sequence having this mutated site is mutated from TATTTT to TAATTT, it was made clear at the same time that a recognition site AATT of a restriction enzyme TspEI (Tsp509I) is produced.

Industrial applicability

The use of the present oligonucleotide as a probe for hybridization analysis or as a primer for a PCR method for amplifying a DNA enables the presence or absence of mutation in a human-derived cytochrome P450IIC18 gene, one of the enzymes participating in the metabolic decomposition of medicines, to be checked. Moreover, such the use leads to higher speed, higher efficiency, higher precision and lower cost in a test and enables the presence or absence of mutation to be readily diagnosed and analyzed before the administration of a medicine. Thus, it becomes possible to determine a safe dose of a medicine which has been difficult to use because of the occurrence of individual difference in drug-metabolizing function and to use also a medicine which takes an active form by the action of this enzyme according to individuals.

What is claimed is:

1. An oligonucleotide for checking the presence or absence of mutation in a human-derived cytochrome P450IIC18 gene, wherein said oligonucleotide comprises up to 500 nucleotides, has a GC content of 40% to 70%, hybridizes with said gene, and has a sequence selected from the group consisting of SEQ ID No:1, SEQ ID No:2, SEQ ID No:3, SEQ ID No:4, SEQ ID No:5, SEQ ID No:6, SEQ ID No:7, SEQ ID No:8, SEQ ID No:9, SEQ ID No:10, SEQ ID No:11, SEQ ID No:12 and SEQ ID No:13.

2. The oligonucleotide of claim 1, which comprises 8 to 50.

3. The oligonucleotide according to claim 2, which has the base sequence shown in SEQ ID No:1.

4. The oligonucleotide according to claim 2, which has the base sequence shown in SEQ ID No:2.

5. The oligonucleotide according to claim 2, which has the base sequence shown in SEQ ID No:3.

6. The oligonucleotide according to claim 2, which has the base sequence shown in SEQ ID No:4.

7. The oligonucleotide according to claim 2, which has the base sequence shown in SEQ ID No:5.

8. The oligonucleotide according to claim 2, which has the base sequence shown in SEQ ID No:6.

9. The oligonucleotide according to claim 2, which has the base sequence shown in SEQ ID No:7.

10. The oligonucleotide according to claim 2, which has the base sequence shown in SEQ ID No:8.

11. The oligonucleotide according to claim 2, which has the base sequence shown in SEQ ID No:9.

12. The oligonucleotide according to claim 1, which has the base sequence shown in SEQ ID No:10.

13. The oligonucleotide according to claim 1, which has the base sequence shown in SEQ ID No:11.

14. The oligonucleotide according to claim 1, which has the base sequence shown in SEQ ID No:12.

15. The oligonucleotide according to claim 1, which has the base sequence shown in SEQ ID No:13.

16. The oligonucleotide of claim 1, 2, 12, 13, 14 or 15, which is labelled with a radioactive or non-radioactive label.

17. A method for detecting a point mutation of T to A at 204 position in exon 2 of human derived cytochrome P450IIC18, which comprises the steps of:

(a) extracting human genomic gene of cytochrome P450IIC18 from a human tissue sample, (b) amplifying the extracted genomic gene by a PCR method, (c) subjecting the amplified DNA fragment to a digestion reaction with a restriction enzyme which recognizes at least an AATT sequence of the mutation site, (d) subjecting the obtained DNA fragment in step (c) to electrophoresis to separate a digested fragment(s) comprising 115 bp or 35 bp or both or a normal wild type fragment to detect the presence of mutation.

18. A method according to claim 17, wherein the PCR reaction is carried out by using a primer which comprises up to 500 nucleotides, which has a GC content of 40% to 70%, which hybridizes with said gene, and which comprises a sequence selected from the group consisting of SEQ ID No:1, SEQ ID No:2, SEQ ID No:3, SEQ ID No:4, SEQ ID No:5, SEQ ID No:6, SEQ ID No:7, SEQ ID No:8, SEQ ID No:9, SEQ ID No:10, SEQ ID No:11, SEQ ID No:12 and SEQ ID No:13.

19. The method according to claim 17, wherein the PCR reaction is carried out by using the primer of SEQ. ID NO. 1 for forward amplification and any one of the primers selected from the group consisting of SEQ ID NO:2, SEQ ID NO:3, SEQ ID NO:4, SEQ ID NO:5, SEQ ID NO:6, SEQ ID NO:7, SEQ ID NO:8 and SEQ ID NO:9 for reverse amplification simultaneously.

20. A method for detecting a point mutation of T to A at 204 position in exon 2 of human derived cytochrome P45IIC18, which comprises the steps of:

(a) extracting human genomic gene of cytochrome P450IIC18 from a human tissue example, (b) digesting the extracted genomic gene with a restriction enzyme which recognizes at least an AATT sequence of the mutation site, (c) separating the digested fragments by electrophoresis, (d) subjecting the separated DNA fragments of interest in step (c) to hybridization using a probe that hybridizes to the digested nucleotide fragment comprising 115 bp or 35 bp, or both of them or the normal wild type fragment derived from an exon 2 region containing the mutation site to detect the presence of the mutation.

21. The method according to claim 20, wherein the extracted human genomic gene is amplified by a PCR method prior to step (b).

22. The method according to claim 17, wherein the PCR in step (b) is carried out by Allele-Specific PCR, PCR direct sequencing, PCR-SSCP or LCR analysis.

23. The method according to claim 20, wherein the hybridization in step (d) is carried out by dot blot hybridization.

24. The method according to claim 17 or 20, wherein the restriction enzyme is Tsp509I.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: Other nucleic acid synthetic DNA ( i i i ) SEQUENCE DESCRIPTION: SEQ ID NO: 1:

TTCTCAAAAG TCTATGGC                                    18

( 2 ) INFORMATION FOR SEQ ID NO:2:

( i ) SEQUENCE CHARACTERISTICS:
        ( A ) LENGTH: 18
        ( B ) TYPE: nucleic acid
        ( C ) STRANDEDNESS: single
        ( D ) TOPOLOGY: linear ( i i ) MOLECULE TYPE: Other nucleic acid synthetic DNA ( i i i ) SEQUENCE DESCRIPTION: SEQ ID NO: 2:

AACTTTTTCA GCCACTGG                                    18

( 2 ) INFORMATION FOR SEQ ID NO:3:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid synthetic DNA ( i i i ) SEQUENCE DESCRIPTION: SEQ ID NO: 3:

TTCAAGCCTG TTTTCCATCC                                  20

( 2 ) INFORMATION FOR SEQ ID NO:4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid synthetic DNA ( i i i ) SEQUENCE DESCRIPTION: SEQ ID NO: 4:

GCAGAACAGA AAACAGAAGC                                  20

( 2 ) INFORMATION FOR SEQ ID NO:5:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: Other nucleic acid synthetic DNA ( i i i ) SEQUENCE DESCRIPTION: SEQ ID NO: 5:

TCCTCGATGC TCCCTCTTCC 20

(2) INFORMATION FOR SEQ ID NO:6:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: Other nucleic acid synthetic DNA (iii) SEQUENCE DESCRIPTION: SEQ ID NO: 6:

TGCAGGGAGC ACAGCCCAGG 20

(2) INFORMATION FOR SEQ ID NO:7:

(i) SEQUENCE CHARACTERISTICS:
        (A) LENGTH: 20
        (B) TYPE: nucleic acid
        (C) STRANDEDNESS: single
        (D) TOPOLOGY: linear (ii) MOLECULE TYPE: Other nucleic acid synthetic DNA (iii) SEQUENCE DESCRIPTION: SEQ ID NO: 7:

AGTCACCCAC CATTGGTTTT 20

(2) INFORMATION FOR SEQ ID NO:8:

(i) SEQUENCE CHARACTERISTICS:
        (A) LENGTH: 15
        (B) TYPE: nucleic acid
        (C) STRANDEDNESS: single
        (D) TOPOLOGY: linear (ii) MOLECULE TYPE: Other nucleic acid synthetic DNA (iii) SEQUENCE DESCRIPTION: SEQ ID NO: 8:

TGATCAATCA GGGCC 15

(2) INFORMATION FOR SEQ ID NO:9:

(i) SEQUENCE CHARACTERISTICS:
        (A) LENGTH: 35
        (B) TYPE: nucleic acid
        (C) STRANDEDNESS: single
        (D) TOPOLOGY: linear (ii) MOLECULE TYPE: Other nucleic acid synthetic DNA (iii) SEQUENCE DESCRIPTION: SEQ ID NO: 9:

GCCCAGTACA TACACATGTA CACATACACA CGATA 35

(2) INFORMATION FOR SEQ ID NO:10:

(i) SEQUENCE CHARACTERISTICS:
        (A) LENGTH: 17
        (B) TYPE: nucleic acid
        (C) STRANDEDNESS: single
        (D) TOPOLOGY: linear (ii) MOLECULE TYPE: Other nucleic acid synthetic DNA (iii) SEQUENCE DESCRIPTION: SEQ ID NO: 10:

CTGTGTAATT TGGCCTG 17

(2) INFORMATION FOR SEQ ID NO:11:

-continued ( i ) SEQUENCE CHARACTERISTICS:
    ( A ) LENGTH: 50
    ( B ) TYPE: nucleic acid
    ( C ) STRANDEDNESS: single
    ( D ) TOPOLOGY: linear ( i i ) MOLECULE TYPE: Other nucleic acid synthetic DNA ( i i i ) SEQUENCE DESCRIPTION: SEQ ID NO: 11:

TTCTCAAAAG TCTATGGCCC TGTGTTCACT GTGTATTTTG GCCTGAAGCC                50

( 2 ) INFORMATION FOR SEQ ID NO:12:

( i ) SEQUENCE CHARACTERISTICS:
        ( A ) LENGTH: 100
        ( B ) TYPE: nucleic acid
        ( C ) STRANDEDNESS: single
        ( D ) TOPOLOGY: linear ( i i ) MOLECULE TYPE: Other nucleic acid synthetic DNA ( i i i ) SEQUENCE DESCRIPTION: SEQ ID NO: 12:

TTCTCAAAAG TCTATGGCCC TGTGTTCACT GTGTATTTTG GCCTGAAGCC CATTGTGGTG     60

TTGCATGGAT ATGAAGCAGT GAAGGAGGCC CTGATTGATC                          100

( 2 ) INFORMATION FOR SEQ ID NO:13:

( i ) SEQUENCE CHARACTERISTICS:
        ( A ) LENGTH: 200
        ( B ) TYPE: nucleic acid
        ( C ) STRANDEDNESS: single
        ( D ) TOPOLOGY: linear ( i i ) MOLECULE TYPE: Other nucleic acid DNA fragment obtained by
            cloning ( i i i ) SEQUENCE DESCRIPTION: SEQ ID NO: 13:

TTCTCAAAAG TCTATGGCCC TGTGTTCACT GTGTATTTTG GCCTGAAGCC CATTGTGGTG     60

TTGCATGGAT ATGAAGCAGT GAAGGAGGCC CTGATTGATC ATGGAGAGGA GTTTTCTGGA    120

AGAGGAAGTT TTCCATTGGC TGAAAAAGTT AACAAAGGAC TTGGTAAATG TGGATGTATC    180

CTGTGTATGT GTACATGTGT                                                200